US00PP32800P3

(12) United States Plant Patent
Larse

(10) Patent No.: US PP32,800 P3
(45) Date of Patent: Feb. 9, 2021

(54) STRAWBERRY PLANT NAMED 'YAKIMA'

(50) Latin Name: ***Fragaria* x *ananassa***
Varietal Denomination: Yakima

(71) Applicant: Sweet Darling Sales, Inc., Aptos, CA (US)

(72) Inventor: John Larse, Watsonville, CA (US)

(73) Assignee: Sweet Darling Sales, Inc., Aptos, CA (US)

( * ) Notice: Subject to any disclaimer, the term of this patent is extended or adjusted under 35 U.S.C. 154(b) by 0 days.

(21) Appl. No.: 16/873,069

(22) Filed: Jan. 28, 2020

(65) Prior Publication Data

US 2020/0245516 P1 Jul. 30, 2020

Related U.S. Application Data

(60) Provisional application No. 62/797,491, filed on Jan. 28, 2019.

(51) Int. Cl.
*A01H 5/08* (2018.01)
*A01H 6/74* (2018.01)

(52) U.S. Cl.
USPC ..... Plt./208
CPC ..... *A01H 6/7409* (2018.05)

(58) Field of Classification Search
USPC ..... Plt./209, 208
CPC ... A01H 5/08; A01H 5/02; A01H 5/00; A01H 6/74; A01H 6/7409
See application file for complete search history.

(56) References Cited

U.S. PATENT DOCUMENTS

PP19,767 P2 2/2009 Shaw et al.
PP25,849 P3 * 9/2015 Larse ..... A01H 6/7409 Plt./209

* cited by examiner

*Primary Examiner* — June Hwu
(74) *Attorney, Agent, or Firm* — Cooley LLP

(57) ABSTRACT

The present invention provides a new and distinct strawberry variety designated as 'Yakima' (a.k.a. '109733'). 'Yakima' is distinguished by its higher percent of marketable fruit, conical fruit shape, thicker canopy and dark green foliage color.

5 Drawing Sheets

Latin name of the genus and species: *Fragaria* x *ananassa.*
Varietal denomination: 'Yakima'.

BACKGROUND OF THE INVENTION

The present invention relates to a new and distinct short-day strawberry variety designated as 'Yakima' (a.k.a. '109733').

'Yakima' (a.k.a. '109733') is the result of a controlled-cross between a female parent cultivar designated ('Aida', a.k.a. '106734',) an unpatented, proprietary strawberry plant variety made by the inventor and a male parent cultivar designated 'Lili' (a.k.a. '101983' or 'Lily', U.S. Plant Pat. No. 25,849) and was first fruited in Watsonville, Calif. growing fields. Following selection and during testing, the plant was originally designated '109733' and subsequently named 'Yakima'.

The new variety was asexually reproduced via runners (stolons) by the inventor at Watsonville, Calif. Asexual propagules from the original source have been tested in Watsonville growing fields and to a limited extent, grower fields in high elevation. The properties of this variety were found to be transmissible by such asexual reproduction. This cultivar is stable and reproduces true to type in successive generations of asexual reproduction.

DESCRIPTION OF THE DRAWINGS

The accompanying color photographs depict various characteristics of the cultivar as nearly true as possible to make color reproductions.

SUMMARY OF THE INVENTION

Figure 1:
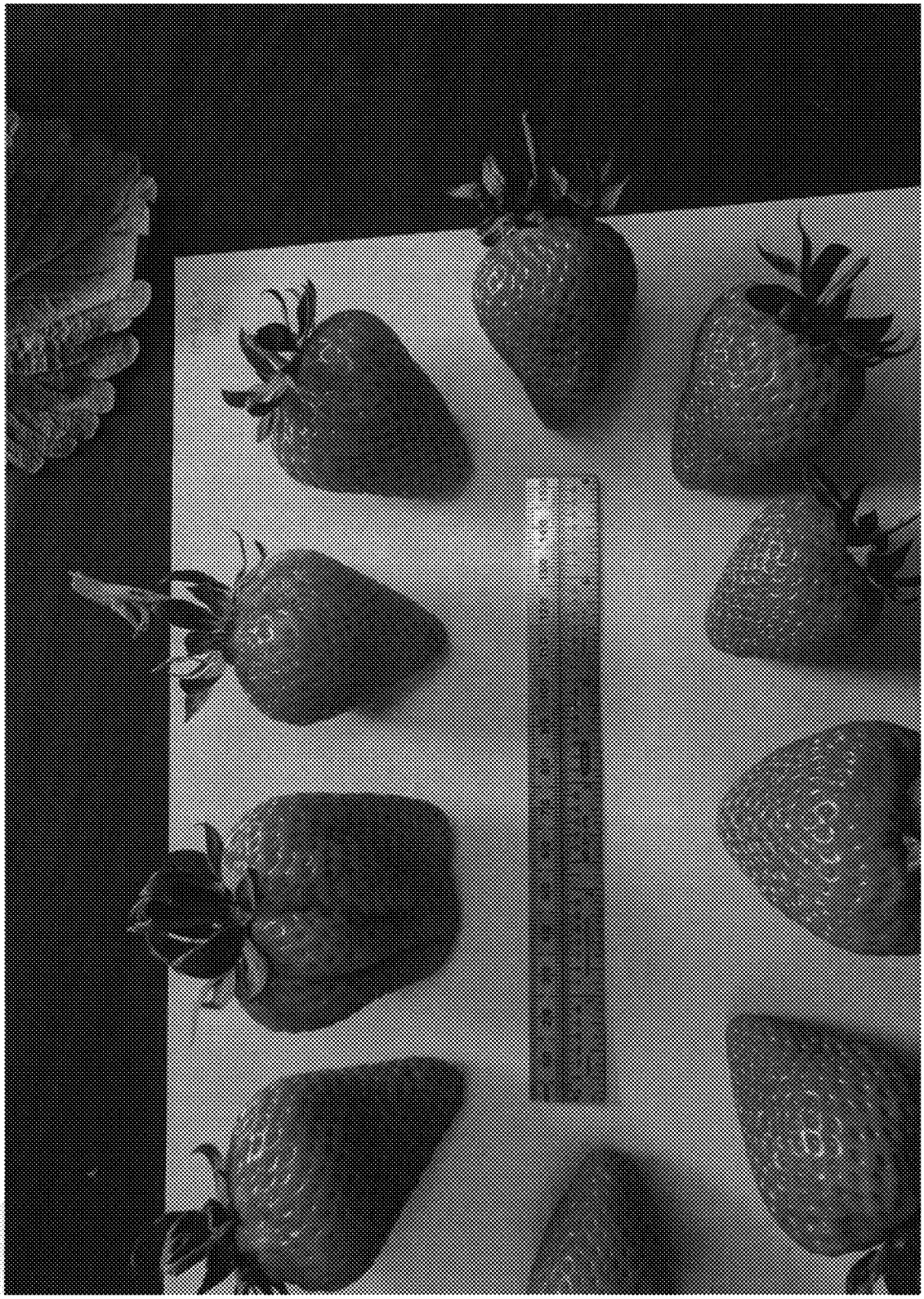
FIG. 1 shows 'Yakima' fruit.
Figure 2:
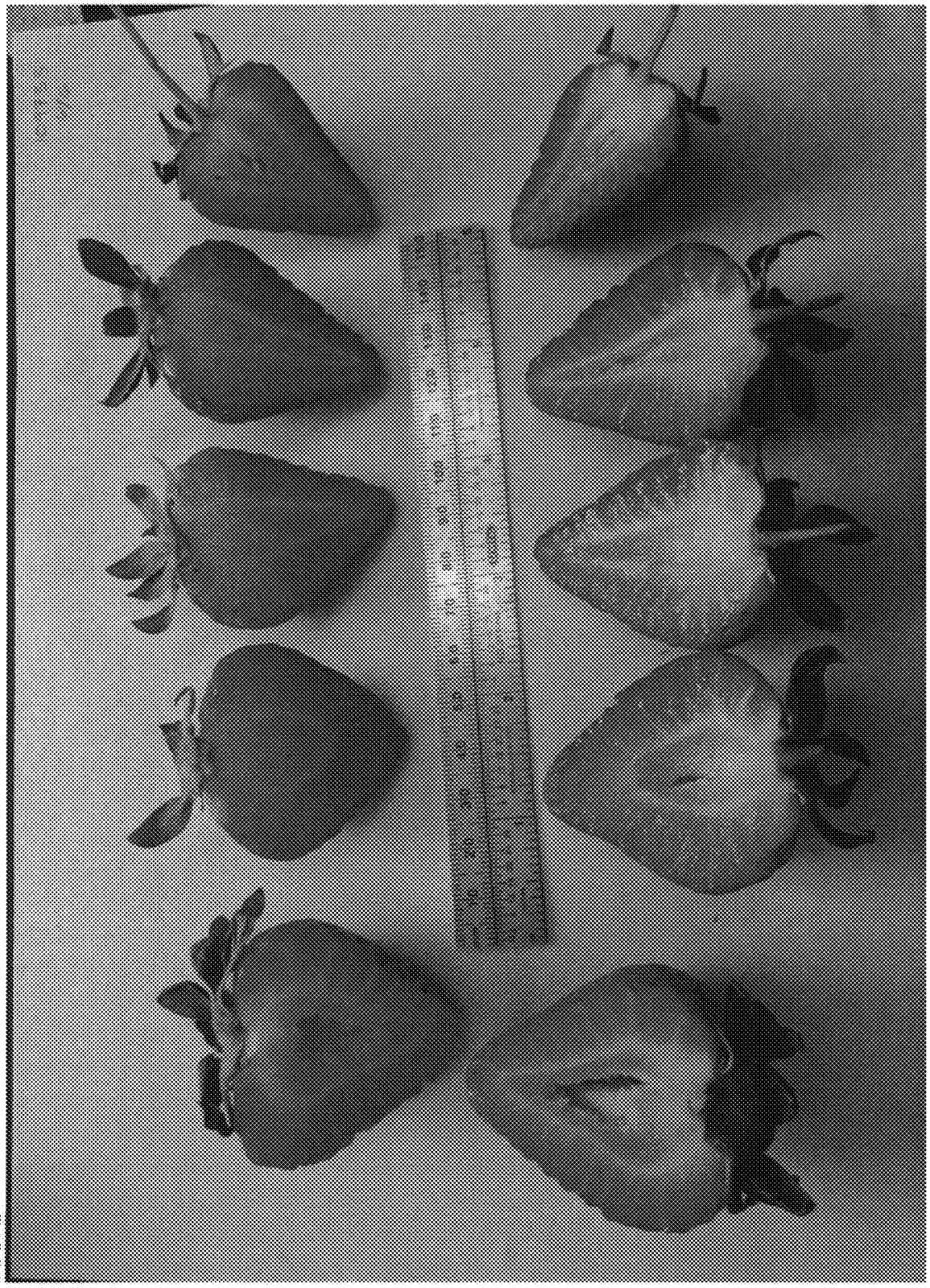
FIG. 2 shows 'Yakima' fruit.
Figure 3A:
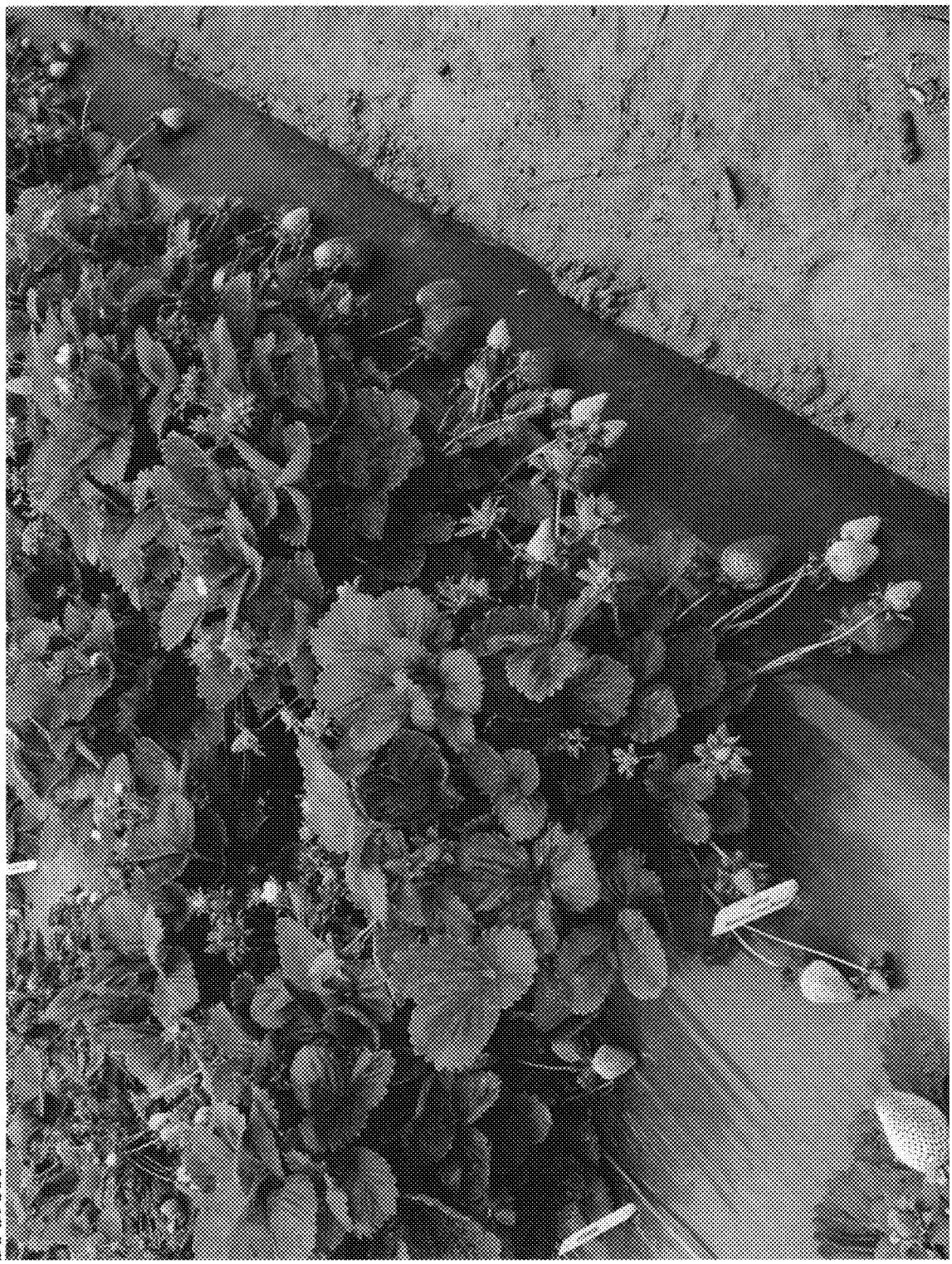
FIG. 3A and FIG. 3B show 'Yakima' strawberry plants with fruit.
Figure 3B:
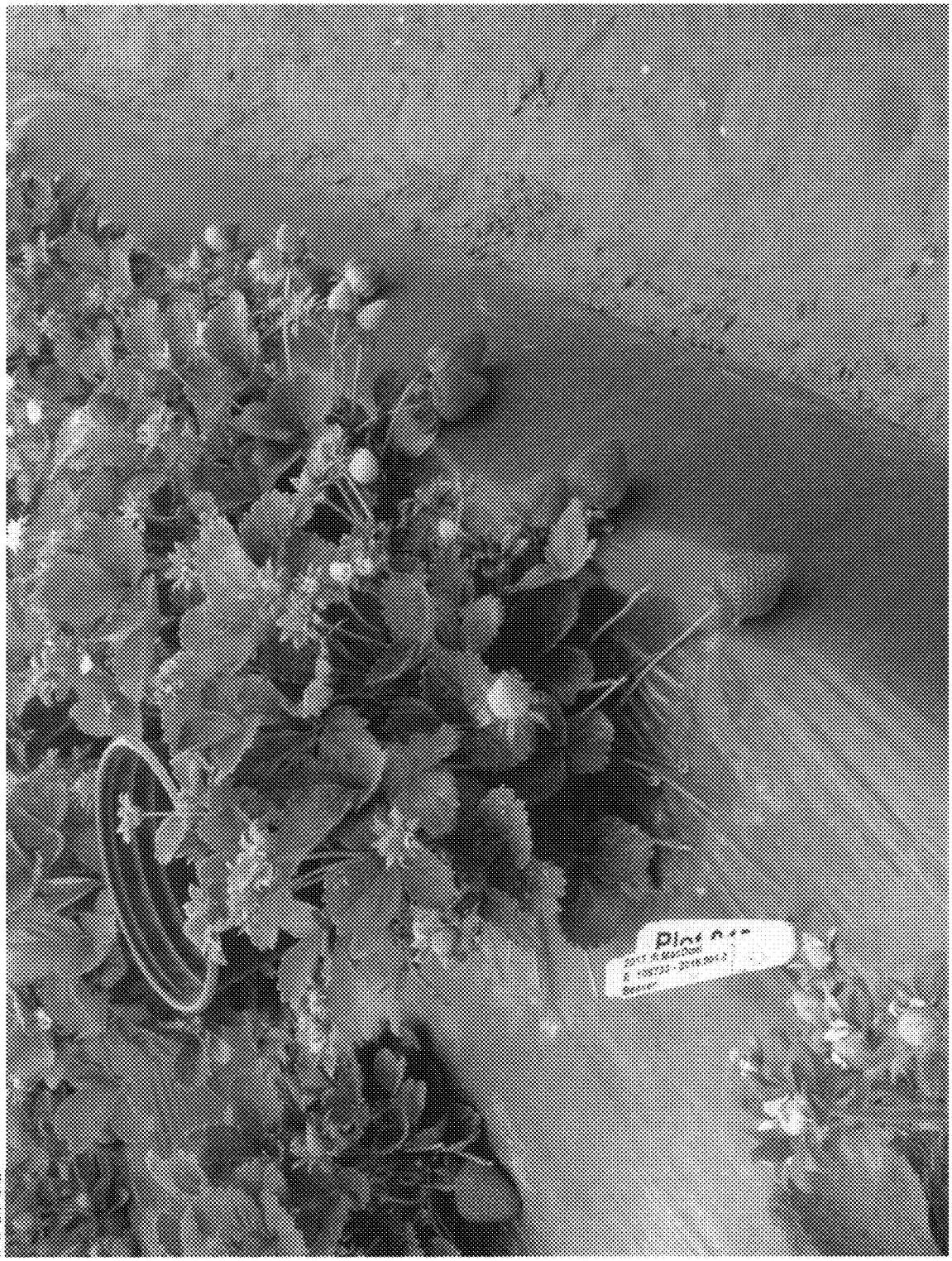
Figure 4:
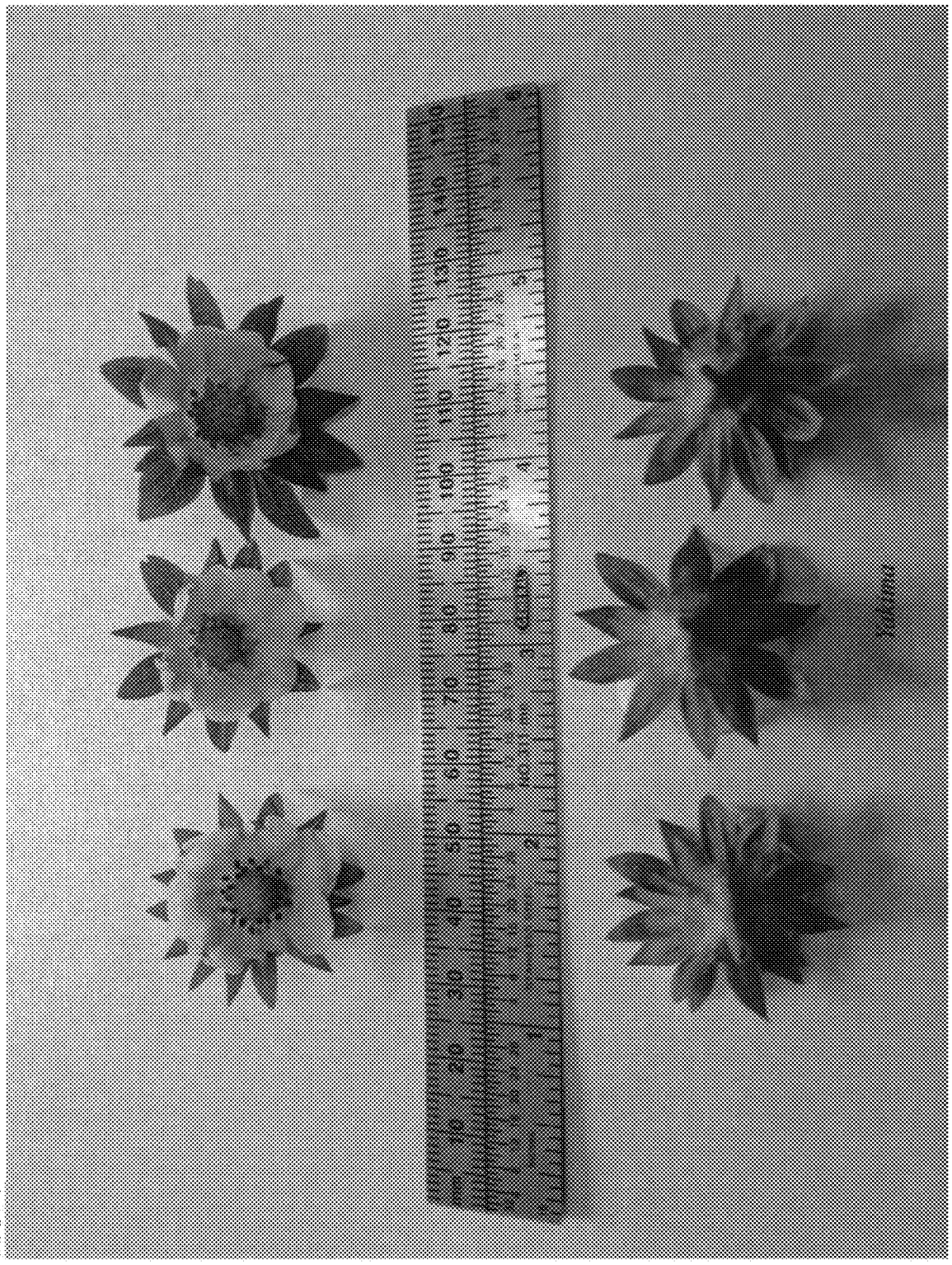
FIG. 4 shows flowers of 'Yakima' strawberry plant variety.

This invention relates to a new and distinctive strawberry cultivar designated as 'Yakima'. This cultivar is primarily adapted to the climate and growing conditions of the central coast of California. This region provides the necessary temperatures required for it to produce a strong vigorous plant and to remain in fruit production from March through October. The nearby Pacific Ocean provides the needed humidity and moderate day temperatures and evening chilling to maintain fruit quality for the production months.

'Yakima' (a.k.a. '109733')

The following traits and photographs in combination distinguish the strawberry variety 'Yakima' from known strawberry varieties. In addition, the new cultivar was confirmed to be a unique strawberry germplasm when tested against the California Seed & Plant Lab, Inc. (Elverta, Calif.) database using Short Sequence Repeats (SSRs). Plants for the botanical measurements in the present application were grown as annuals. Any color references are made to The Royal Horticultural Society Colour Chart, 1995 Edition, except where general terms of ordinary dictionary significance are used. The botanical measurements listed in Table 1 were made and recorded during the month of June.

'Yakima' is distinguished from its paternal parent by the percent of marketable fruit (Table 2), for 'Yakima' percent marketable fruit is twenty percentile points greater than its paternal parent 'Lili' (U.S. Plant Pat. No. 25,849). 'Yakima' is distinguished from its maternal parent 'Aida' by the shape of its fruit. The fruit of 'Yakima' is mostly conical, different from the longer somewhat flat wedge shape of the fruit of its parent 'Aida'. 'Yakima' is similar to the strawberry plant named 'Monterey' (U.S. Plant Pat. No. 19,767), but possesses several distinguishing traits from Monterey. 'Yakima' is distinguished from 'Monterey' by the thicker canopy of 'Yakima' and dark green foliage color of 'Yakima'.

TABLE 1

| Characteristic Type | Characteristic | Yakima |
|---|---|---|
| General | Plant Habit | annual |
| | Plant Growth Habit | upright |
| | Day length | short-day |
| | Planting season | Fall |
| | Height | 35 cm |
| | Width | 36 cm |
| | Density of foliage | medium |
| | Plant vigor | high |
| | Freezing Quality | moderate |
| | Rain/weather tolerance | moderate to high |
| | Harvest Ease | moderate |
| Leaf | Leaf Shape | concave |
| | Terminal leaflet width | 90 mm |
| | Terminal leaflet length | 100 mm |
| | Terminal leaflet length/width ratio | 1.11 |
| | Teeth per terminal leaflet | 17 to 19 |
| | Shape of terminal leaflet base | rounded |
| | Shape of terminal leaflet in cross-section | concave to straight |
| | Shape of terminal leaflet margin | serrate to crenate |
| | Color of upper side of leaflet | RHS 136A |
| | Color of lower side of leaflet | RHS 139C |
| | Leaf blistering | weak |
| | Leaf glossiness | medium |
| | Leaf variegation | absent |
| | Number of leaflets | 3 leaflets per leaf |
| | Leaf length | 133 mm |
| | Leaf width | 151 mm |
| | Terminal Leaflet margin | revolute |
| | Terminal Leaflet shape | Orbicular |
| | Terminal Leaflet shape of apex | Rounded |
| Limbs | Petiole length | 25.5 cm |
| | Petiole diameter | 3.18 to 4.26 mm |
| | Petiole pubescence | medium |
| | Petiole pose of hairs | horizontal |
| | Petiole color | RHS 145A |
| | Petiolule length | 1.0 to 1.5 cm |
| | Petiolule diameter | 2.08 to 2.70 mm |
| | Stipule length | 3.5 cm |
| | Stipule width | 0.9 to 1.0 cm |
| | Stipule pubescence | dense |
| | Stipule anthocyanin | absent |
| | Stipule color (color code) | RHS 145C |
| | Pedicel color (color code) | RHS 145A |
| | Attitude of hairs on peduncle and pedicel | horizontal to slightly upwards |
| | Peduncle length | 19.5 cm |
| | Pedicel length | 13.8 cm |
| Inflorescence | Inflorescence position relative to foliage | above |
| | Flower arrangement of petals | touching |
| | Flower size | medium |
| | Flower diameter | 2.28 cm |
| | Petal shape | orbicular |
| | Petal apex | rounded |
| | Petal margin | entire |
| | Petal base shape | concave |
| | Petal length | 1.17 cm |

TABLE 1-continued

| Characteristic Type | Characteristic | Yakima |
|---|---|---|
| | Petal width | 1.15 cm |
| | Petal length/width ratio | 1.02 |
| | Petal number per flower | 5 to 7 |
| | Number of flowers | 16 to 36 |
| | Upper Petal color | RHS 155D |
| | Lower Petal color | RHS 155D |
| | Floral Calyx Diameter | 4.08 cm |
| | Corolla diameter | 2.28 cm |
| | Calyx diameter relative to corolla | larger |
| | Inner calyx | Outer calyx and inner calyx are of equal size |
| | Sepal shape | elliptical |
| | Sepal apex shape | acute |
| | Sepal margin | entire |
| | Sepal length | 1.93 cm |
| | Sepal width | 0.61 cm |
| | Sepal number per flower | 12 |
| | Upper Sepal color | RHS 137A |
| | Lower Sepal color | RHS 137C |
| | Receptacle color | RHS 4A |
| | Fertility | not tested |
| | Time of flowering (50% of plants in bloom) | May |
| | Stigma shape | rounded |
| | Stigma color | RHS 4A |
| | Style length | 5 mm |
| | Style color | RHS 4A |
| | Ovary color | RHS 138D |
| | Stamen number | 25 |
| | Stamen length | 2.3 mm |
| | Anther shape | dorsifixed |
| | Anther shape | 1.39 mm |
| | Anther color | RHS 6A |
| | Pollen amount | scarce to moderate |
| | Pollen color | RHS 163B |
| | Filament color | RHS 145C |
| | Filament length | 1.2 to 2.8 mm |
| Fruit | Fruiting truss length | 6 to 17 cm |
| | Fruiting truss diameter | 1.4 mm |
| | Number of fruit per truss | 1 to 5 |
| | Fruit length | 5.3 cm |
| | Fruit width | 4.3 cm |
| | Fruit skin color | RHS 45A |
| | Fruit flesh color excluding core | RHS 44A |
| | Fruit core color | RHS 41B |
| | Fruit length/width ratio | 1.23 |
| | Fruit weight | 33 g |
| | Relative fruit size | medium to large |
| | Predominant fruit shape | long conic and long wedge |
| | Shape difference between primary & secondary fruits | No shape difference |
| | Width of band without of achenes | narrow |
| | Fruit glossiness | strong |
| | Position of achenes | below surface |
| | Achene color | RHS 151D |
| | Achenes per fruit | 340 |
| | Achene weight | 0.238 g |
| | Position of calyx | even |
| | Fruit Calyx Diameter | 5.5 cm |
| | Level of adherence of calyx | medium |
| | Color of calyx | RHS 137C |
| | Pose of calyx segments | reflexed |
| | Size of calyx in relation to fruit | same |
| | Firmness of flesh | medium to firm |
| | Evenness of flesh color | nearly even |
| | Fruit hollow length | 2.3 cm |
| | Fruit hollow width | 1.4 cm |
| | Fruit hollow length/width ratio | 1.64 |
| | Hollow center | absent to medium |
| | Sweetness | 7 to 14 Brix |

TABLE 1-continued

| Characteristic Type | Characteristic | Yakima |
|---|---|---|
| | pH | 3.33 |
| | Texture when tasted | fine to medium |
| | Time of flowering | April through August |
| | Time of fruit ripening | May |
| | Harvest maturity (50% of plants with ripe fruit) | June |
| | Type of bearing | short-day |
| | Grams of fruit per plant | June: 721 g |
| | Yield (lb per acre) | June: 31,791 lb/acre |
| | Firmness | medium to firm |
| | Surface Texture | smooth |
| | Appearance Score (rating scale 1 to 5; 5 = best) | 4 |
| | Storage longevity | 5 to 10 days |
| | Cull rate: 1% Usable | <10% |
| Stolon | Stolon number | 1 to 3 |
| | Stolon length from crown to first daughter | 22.4 cm |
| | Pubescence density | dense |
| | Intensity of anthocyanin coloration | absent |
| | Stolon color | RHS N144D |
| Disease Resistance | Plant/fruit disease | resistant to Fusarium wilt |
| | Pest resistance/susceptibility | resistant to *Fusarium oxysporum* f. sp. *fragariae*; susceptible to *Colletotrichum acutatum* |
| Other characteristics | Plant hardness zone | USDA hardiness zone 9b |
| | Shipping quality and fruit market use | The fruit of the Yakima strawberry plant is suitable for shipping and merchandising for distant commercial markets. |

TABLE 1-continued

| Characteristic Type | Characteristic | Yakima |
|---|---|---|
| | Short-day designation | Differentiation of new florescence is required for a prior period of vernalization. (short-day genotype) |

TABLE 2

Strawberry fruit summary statistic means of yield, percent marketable, flavor, firmness, figure and size during weeks 15 to 37 over years; Watsonville, California.

| Variety | Mean fruit height (fHeight) | Mean fruit width (fWidth) | Mean fruit height/width (fHeight/fWidth) | Mean hardness in Newtons (N) (μ hardness) | Mean grams per clone (μ grams/clone) |
|---|---|---|---|---|---|
| Yakima | 51.0304 | 40.2999 | 1.26626 | 8.79292 | 1622 |
| Lili | 40.2262 | 35.8540 | 1.12194 | 8.78205 | 1304 |

| Variety | Mean Kilos/acre (μ kilos/acre) | Mean percent of marketable fruit (μ % Usable) | Mean fruit size in Grams (μ frtSizeGrms) | Mean skin-resistance-to-abrasion categorical rating (μ skin-r) | Mean categorical flavor rating (μ flavor) |
|---|---|---|---|---|---|
| Yakima | 32,443 | 0.905 | 31.39 | 2.13004 | 2.84304 |
| Lili | 26,089 | 0.797 | 29.95 | 2.09745 | 3.05084 |

The invention claimed is:

1. A new and distinct cultivar of strawberry plant named 'Yakima' substantially as shown and described herein.

* * * * *